US006717136B2

(12) United States Patent
Andersson et al.

(10) Patent No.: US 6,717,136 B2
(45) Date of Patent: Apr. 6, 2004

(54) MICROFLUDIC SYSTEM (EDI)

(75) Inventors: Per Andersson, Uppsala (SE); Helene Derand, Taby (SE); Magnus Gustafsson, Solna (SE); Anders Palm, Uppsala (SE); Sussanne Wallenborg, Uppsala (SE)

(73) Assignee: Gyros AB, Uppsala (SE)

( * ) Notice: Subject to any disclaimer, the term of this patent is extended or adjusted under 35 U.S.C. 154(b) by 376 days.

(21) Appl. No.: 09/812,123

(22) Filed: Mar. 19, 2001

(65) Prior Publication Data

US 2002/0142481 A1 Oct. 3, 2002

(51) Int. Cl.[7] ................................................ B01D 15/08
(52) U.S. Cl. ...................... 250/288; 250/281; 422/70; 422/68.1; 422/100; 210/198.2; 210/657
(58) Field of Search ................ 250/288, 281, 250/282; 422/70, 68.1, 100; 210/198.2, 659

(56) References Cited

U.S. PATENT DOCUMENTS

| | | |
|---|---|---|
| 3,852,595 A | 12/1974 | Aberth |
| 4,279,862 A | 7/1981 | Bretaudiere et al. |
| 4,465,935 A | 8/1984 | von Criegern et al. |
| 4,879,458 A | 11/1989 | Brunfeldt et al. |
| 5,115,131 A | 5/1992 | Jorgenson et al. |
| 5,197,185 A | 3/1993 | McCoy et al. |
| 5,310,523 A | 5/1994 | Smethers et al. |
| 5,608,519 A | 3/1997 | Gourley et al. |
| 5,637,469 A | 6/1997 | Wilding et al. |
| 5,705,813 A | 1/1998 | Apffel et al. |
| 5,716,825 A * | 2/1998 | Hancock et al. .......... 435/286.5 |
| 5,866,345 A | 2/1999 | Wilding et al. |
| 5,872,010 A | 2/1999 | Karger et al. |
| 5,905,258 A | 5/1999 | Clemmer et al. |
| 5,969,353 A | 10/1999 | Hsieh |
| 6,063,589 A | 5/2000 | Kellogg et al. |
| 6,110,343 A | 8/2000 | Ramsey et al. |

(List continued on next page.)

FOREIGN PATENT DOCUMENTS

| | | |
|---|---|---|
| EP | 0 073 513 B1 | 8/1982 |
| EP | 0 073 513 B2 | 8/1982 |
| EP | 0 073 513 A1 | 8/1982 |
| EP | 0-655 618 A2 | 5/1995 |
| WO | WO/97/04297 | 2/1997 |
| WO | 97/21090 A1 | 6/1997 |
| WO | 97/21090 | 6/1997 |
| WO | 00/30167 A1 | 5/2000 |
| WO | WO-00/40750 A1 | 7/2000 |
| WO | 00/50172 | 8/2000 |
| WO | 00/67293 A1 | 11/2000 |
| WO | WO 01/47637 A1 | 7/2001 |
| WO | WO/01/54810 A1 | 8/2001 |
| WO | 01/63241 A2 | 8/2001 |

OTHER PUBLICATIONS

Zhang, B. et al. Microfabricated Devices for Capillary Electrophoresis–Electrospray Mass Spectrometry; Analytical Chemistry, vol. 71, No. 15, Aug. 1, 1999 pp. 3258–3264.

Kido, H. et al, Disc–based Immunoassay Microarrays; Analytica Chimica Acta 411 (2000).

*Primary Examiner*—Nikita Wells
(74) *Attorney, Agent, or Firm*—Fulbright & Jaworski, L.L.P.

(57) ABSTRACT

A microfluidic device comprising an MS-analyte presentation unit for a EDI-MS apparatus, said unit comprising an essentially planar support plate which on one side has one, two or more ports (MS-ports) comprising an area (EDI area) for presenting the MS-analyte to a mass spectrometer. The EDI area comprises a layer I of conducting material. The characteristic feature of the device is that layer (I) has a conductive connection and/or that there is a calibrator area in the proximity of the MS-port.

11 Claims, 7 Drawing Sheets

U.S. PATENT DOCUMENTS

| | | |
|---|---|---|
| 6,143,247 A | 11/2000 | Sheppard, Jr. et al. |
| 6,302,134 B1 | 10/2001 | Kellogg et al. |
| 6,319,468 B1 | 11/2001 | Sheppard, Jr. et al. |
| 6,319,469 B1 | 11/2001 | Mian et al. |
| 6,326,083 B1 | 12/2001 | Yang et al. |
| 6,459,080 B1 * | 10/2002 | Yin et al. ............ 250/288 |
| 2001/0055812 A1 | 12/2001 | Mian et al. |
| 2002/0118355 A1 | 8/2002 | Worthington et al. |
| 2003/0066957 A1 | 4/2003 | Andersson et al. |
| 2003/0066959 A1 | 4/2003 | Andersson et al. |

* cited by examiner

MICROFLUDIC SYSTEM (EDI)

TECHNICAL FIELD

The present invention relates to a microfluidic device, which can be interfaced to a mass spectrometer (MS). The device comprises a microchannel structure having a first port (inlet port) and a second port (outlet port). A sample to be analysed is applied to the first port and presented to the mass spectrometer in the second port. This second port will be called an MS-port. There may be additional inlet and outlet ports. During passage through the microchannel structure the sample is prepared to make it suitable for analysis by mass spectrometry.

The sample presented in an MS-port will be called an MS-sample. An analyte in an MS-sample is an MS-analyte. "Sample" and "analyte" without prefix will primarily refer to a sample applied to an inlet port.

One important aspect of the present invention concerns mass spectrometry in which the MS-samples are subjected to Energy Desorption/Ionisation from a surface by input of energy. Generically this kind of process will be called EDI and the surface an EDI surface in the context of the invention. Typicallly EDIs are thermal desorption/ionisation (TDI), plasma desorption/ionisation (PDI) and various kinds of irradiation desorption/ionisation (IDI) such as by fast atom bombardment (FAB), electron impact etc. In the case a laser is used the principle is called laser desorption/ionisation (LDI). Desorption may be assisted by presenting the MS analyte together with various helper substances or functional groups on the surface. Common names are matrix assisted laser desorption/ionisation (MALDI) including surface-enhanced laser desorption/ionisation (SELDI). For MALDI see the publications discussed under Background Publications below. For SELDI see WO 0067293 (Ciphergen Biosystems).

The surface from which desorption/ionisation is intended to take place is called an EDI surface.

By microformat is meant that in least a part of the microchannel structures the depth and/or width is in the microformat range, i.e. $<10^3$ μm, preferably $<10^2$ μm. In the most typical microformat structures either the width and/or the depth are in principle within these ranges essentially everywhere between the sample inlet port and the MS-port.

BACKGROUND PUBLICATIONS

For some time there has been a demand for microfluidic sample handling and preparation devices with integrated MS-ports. This kind of devices would facilitate automation and parallel experiments, reduce loss of analyte, increase reproducility and speed etc.

WO 9704297 (Karger et al) describes a microfluidic device that has an outlet port that is claimed useful when conducting electrospray ionisation mass spectrometry (ESI MS), atmospheric pressure chemical ionisation mass spectrometry (APCI MS), matrix assisted laser desorption/ionisation mass spectrometry (MALDI MS) and a number of other analytical principles.

U.S. Pat. No. 6,110,343 (Ramsey et al) describes an electrospray interface between a microfluidic device and a mass spectrometer.

U.S. Pat. No. 5,969,353 (Hsieh) describes an improved interface for electrospray ionization mass spectrometry. The interface is in the form of an electrospray tip connected to a microchannel structure of a chip.

U.S. Pat. No. 5,197,185 (Yeung et al) describes a laser-induced vaporisation and ionization interface for directly coupling a microscale liquid based separation process to a mass spectrometer. A light-adsorbing component may be included in the eluting liquid in order to facilitate vaporisation.

U.S. Pat. No. 5,705,813 (Apffel et al) and U.S. Pat. No. 5,716,825 (Hancock et al) describe a microfluidic chip containing an interface between a microfluidic device and an MALDI-TOF MS apparatus. The microfluidic device comprises
  (a) an open ionisation surface that may be used as the probe surface in the vaccum gate of an MALDI-TOF MS apparatus (column 6, lines 53–58 of U.S. Pat. No. 5,705,813) or
  (b) a pure capture/reaction surface from which the MS-analyte can be transferred to a proper probe surface for MALDI-TOF MS (column 12, lines 13–34, of U.S. Pat. No. 5,716,825).

These publications suggest that means, such as electrical connections, pumps etc, for transporting the liquid within a microchannel structure of the device are integrated with or connected to the device. This kind of transporting means imposes an extra complexity on the design and use, which in turn may negatively influence the production costs, easiness of handling etc of these devices.

U.S. Pat. No. 5,705,813 (Apffel et al) and U.S. Pat. No. 5,716,825 (Hancock et al) are scarce about
  the proper fluidics around the MALDI ionisation surface,
  the proper crystallisation on the MALDI ionisation surface,
  the proper geometry of the port in relation to crystallisation, evaporation, the incident laser beam etc,
  the proper arrangement of conductive connections to the MALDI ionisation surface for MALDI MS analysis.

WO 04297 (Karger et al) and WO 0247913 (Gyros AB) suggest to have microchannel structures in radial or spoke arrangement.

A number of publications referring to the use of centrifugal force for moving liquids within microfluidic systems have appeared during the last years. See for instance WO 9721090 (Gamera Bioscience), WO 9807019 (Gamera Bioscience) WO 9853311 (Gamera Bioscience), WO 9955827 (Gyros AD), WO 9958245 (Gyros AD), WO 0025921 (Gyros AB), WO 0040750 (Gyros AB), WO 0056808 (Gyros AB), WO 0062042 (Gyros AD) and WO 0102737 (Gyros AB) as well as WO 0147637 (Gyros AB), WO 0154810 (Gyros AB), WO 0147638 (Gyros AB), and WO 01411465.

See also Zhang et al, "Microfabricated devices for capillary electrophoresis—electrospray mass spectrometry", Anal. Chem. 71 (1999) 3258–3264) and references cited therein.

Kido et al., ("Disc-based immunoassay microarrays", Anal. Chim. Acta 411 (2000) 1–11) has described microspot immunoassays on a compact disc (CD). The authors suggest that a CD could be used as a continuous sample collector for microbore HPLC and subsequent detection for instance by MALDI MS. In a preliminary experiment a piece of a CD manufactured in polycarbonate was covered with gold and spotted with a mixture of peptides and MALDI matrix.

OBJECTS OF THE INVENTION

A first object is to provide improved means and methods for transporting samples, analytes including fragments and derivatives, reagents etc in microfluidic devices that are capable of being interfaced with a mass spectrometer.

A second object is to provide improved microfluidic methods and means for sample handling before presentation of a sample analyte as an MS-analyte. Sub-objects are to provide an efficient concentration, purification and/or transformation of a sample within the microfluidic device while maintaining a reproducible yield/recovery, and/or minimal loss of precious material.

A third object is to provide improved microfluidic methods and means that will enable efficient and improved presentation of the MS-sample/MS-analyte. This object in particular applies to MS-samples that are presented on a surface, i.e. an EDI surface.

A fourth object is to enable reproducible mass values from an MS-sample that is presented on a surface, i.e. on an EDI surface.

A fifth object is to provide improved microfluidic means and methods for parallel sample treatment before presentation of the analyte to mass spectrometry. The improvements of this object refer to features such as accuracy in concentrating, in chemical transformation, in required time for individual steps and for the total treatment protocol etc. By parallel sample treatment is meant that two or more sample treatments are run in parallel, for instance more than five, such as more than 10, 50, 80, 100, 200, 300 or 400 runs. Particular important numbers of parallel samples are below or equal to the standard number of wells in microtiter plates, e.g. 96 or less, 384 or less, 1536 or less, etc A sixth object is to provide a cheap and disposable microfluidic device unit enabling parallel sample treatments and having one or more MS-ports that are adapted to a mass spectrometer.

SUMMARY OF THE INVENTION

The present inventors have recognized that several of the above-mentioned objects can be met in the case inertia force is used for transportation of a liquid within a microfluidic device of the kind discussed above. This is applicable to any liquid that is used in the microfluidic device, for instance washing liquids and liquids containing at least one of (a) the analyte including derivatives and fragments thereof, (b) a reagent used in the transformation of the sample/analyte, etc.

The present inventors have also recognized that one way of optimizing an EDI area within a microfluidic device is related to (a) the design and/or positioning of a conducting layer in the EDI area, and/or (b) the importance of a conductive connection to the EDI area for MS analysis.

This kind of connection supports the proper voltage and/or charge transport at the EDI area, for instance.

Improper conductive properties may interfere with the mass accuracy, sensitivity, resolution etc.

Conductive and non-conductive properties shell refer to the property of conducting electricity.

A first aspect of the invention is thus a method for transforming a liquid sample containing an analyte to an MS-sample containing an MS-analyte and presenting the MS-sample to a mass spectrometer. The method is characterized in comprising the steps of:

(a) applying the liquid sample to an inlet port of a covered microchannel structure of a microfluidic device, (b) transforming the liquid sample to an MS-sample containing the MS-analyte within the microchannel structure, and (c) presenting the MS-analyte to the mass spectrometer.

A further characteristic feature of this aspect is that transport of liquid within the microchannel structure is performed by the application of inertia force. Inertia force may be the driving force in only a part of the microchannel structure or the whole way from an inlet port to an MS-port and/or to any other outlet port. It is believed that the most general and significant advantages of using inertia force will be accomplished in so called transporting zones, i.e. between zones having predetermined functionalities, or for overcoming or passing through valve functions within a microchannel structure (capillary junctions, hydrophobic breaks etc). See below. The MS-port typically has a conductive connection for MS analysis.

At the priority date the most important inertia force for microfluidic devices is centrifugal force. In other words a force that causes outward radial transportation of liquid by spinning a disc in which the liquid is located within microchannel structures that are oriented radially (spinning is around an axis that is perpendicular to the plane of the disc). Inertia force caused by other changes of direction and/or magnitude of a force can be utilized.

The first aspect also includes the corresponding mass spectrometric method, i.e. the same method together with the actual collection of a mass spectrum and analysis thereof, for instance in order to gain molecular weight and structure information about the analyte.

The first aspect is further defined as discussed below for the microfluidic device as such and for the individual steps.

A second aspect of the invention is a microfluidic device containing one, two or more microchannel structures containing an inlet port, an MS-port and a flow path connected to one or both of the ports. The device may be disc-formed or otherwise provide a planar form. The characteristic feature is that the microchannel structures are oriented radially in an annular/circular arrangement. Thus each microchannel structure extends in a radial direction with an inlet port at an inner position and an outlet port such as an MS-port, at an outer peripheral position. The MS-port typically has a conductive connection as discussed above. The features discussed below further define this aspect of the invention.

A third aspect of the invention is a microfluidic device comprising a plurality of covered microchannel structures as defined herein and with each microchannel structure having an MS-port comprising an EDI area in which there is a conducting layer (layer I). This aspect of the present invention comprises a number of subaspects having the common characteristic feature that there may be a conductive connection to layer (I) of each individual EDI area, as discussed above. There are also features that are distinct for each subaspect.

A first subaspect is further characterized in that layer (I) of each EDI area is part of a continuous conducting layer that is common for two or more up to all of the EDI-areas.

A second subaspect is further characterized in that in each EDI area there is a non-conducting layer (layer II) between layer (I) and the surface of the EDI area. Layer (II) in each EDI area may be part of a continuous non-conducting layer that is common for two or more up to all of the EDI-areas.

A third subaspect is further characterised in that each MS-port has an opening that is restricted by a lid which is common for and covers a number of microchannel structures. The lid may have a conducting layer that at least embraces the openings that are present in the lid. The conducting layer may be continuous in the sense that it covers at least the areas around and between the openings of two or more up to all of the MS-ports. This layer may have a conductive connection as discussed above.

A fourth subaspect is similar to the third subaspect in the sense that there is a lid covering at least a part of each microchannel structures. In this subaspect the lid also covers or restricts the openings of the MS-ports and is removable to an extent that enables exposure of the opening in each MS-port, for instance exposing the surfaces of EDI areas. For EDI ports the removal will facilitate irradiation and the desorption/ionisation of the MS-analyte. The removal may also facilitate evaporation of volatile components.

THE SAMPLE

The sample applied to an inlet port may contain one or more analytes, which may comprise lipid, carbohydrate, nucleic acid and/or peptide structure or any other inorganic or organic structure. The sample treatment protocol to take place within the microchannel structure typically means that the sample is transformed to one or more MS-samples in which (a) the MS-analyte is a derivative of the starting analyte and/or (b) the amount(s) of non-analyte species have been changed compared to the starting sample, and/or (c) the relative occurrence of different MS-analytes in a sample is changed compared to the starting sample, and/or (d) the concentration of an MS-analyte is changed relative the corresponding starting analyte in the starting sample, and/or (e) sample constituents, such as solvents, have been changed and/or the analyte has been changed from a dissolved form to a solid form, for instance in a co-crystallized form.

Item (a) includes digestion into fragments of various sizes and/or chemical derivatization of an analyte. Digestion may be purely chemical or enzymatic. Derivatization includes so-called mass tagging of either the starting analyte or of a fragment or other derivative formed during a sample treatment protocol, which takes place in the microchannel structure. Items (b) and/or (c) include that the sample analyte has been purified and/or concentrated. Items (a)–(d), in particular, apply to analytes that are biopolymers comprising carbohydrate, nucleic acid and/or peptide structure.

The sample is typically in liquid form and may be aqueous.

The sample may also pass through the microchannel structure without being changed. In this case the structure only provide a proper form for dosing of the analyte to the mass spectrometer.

FIGURES

FIGS. 5a–f illustrate various design and positions of the conducting layer (I) in MS-ports containing an EDI area (cross-sectional sideview of two ms ports). The microfluidic device is fabricated in a planar substrate.

Figure 6:
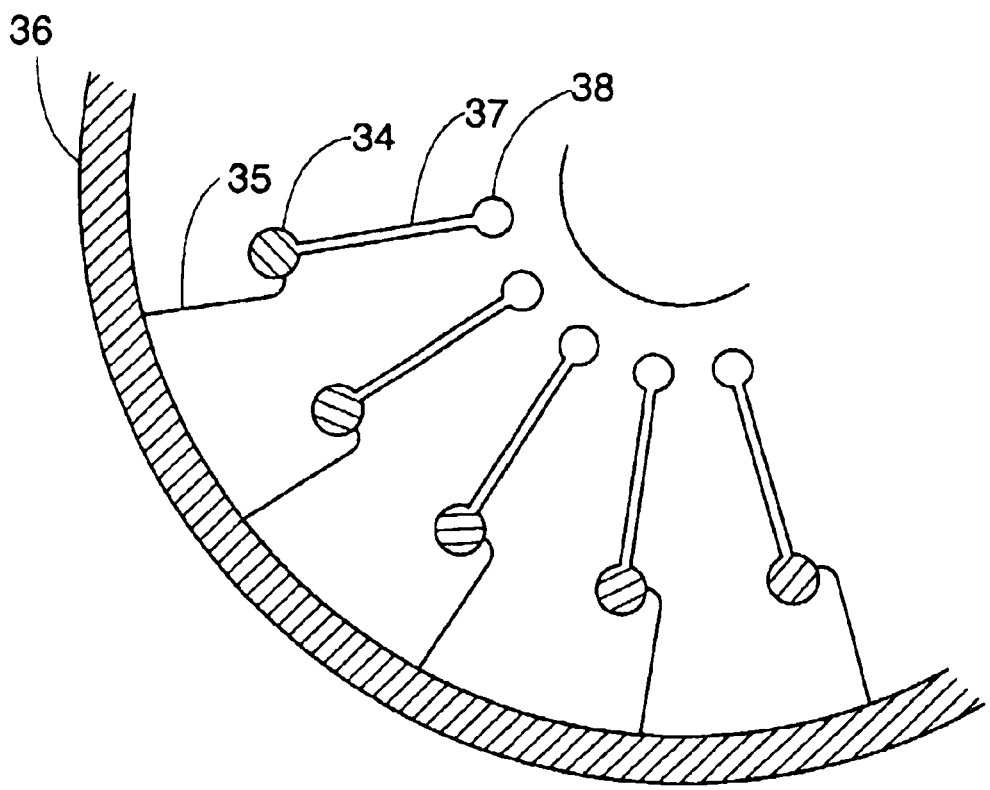

FIG. 6 illustrates an arrangement around EDI MS-ports with layer (I) and conductive connections (transparent lid, seen from above).

Figure 7A:
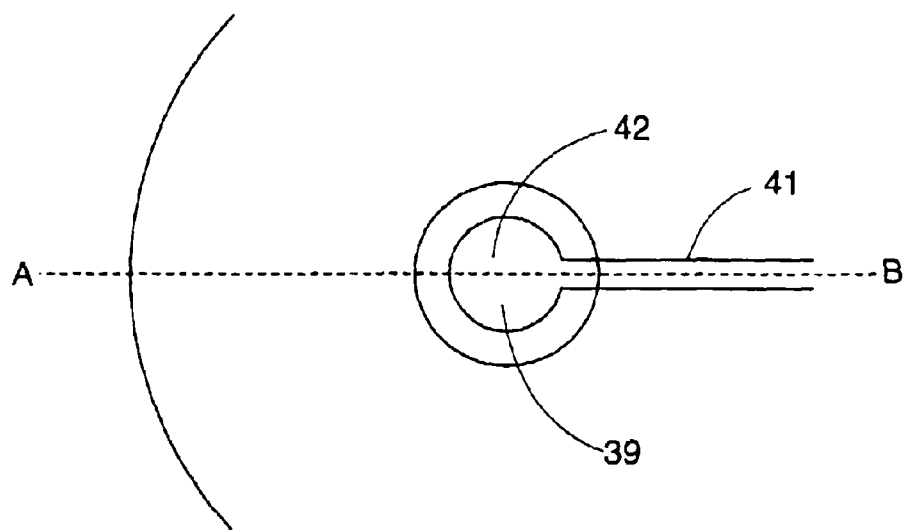
Figure 7B:
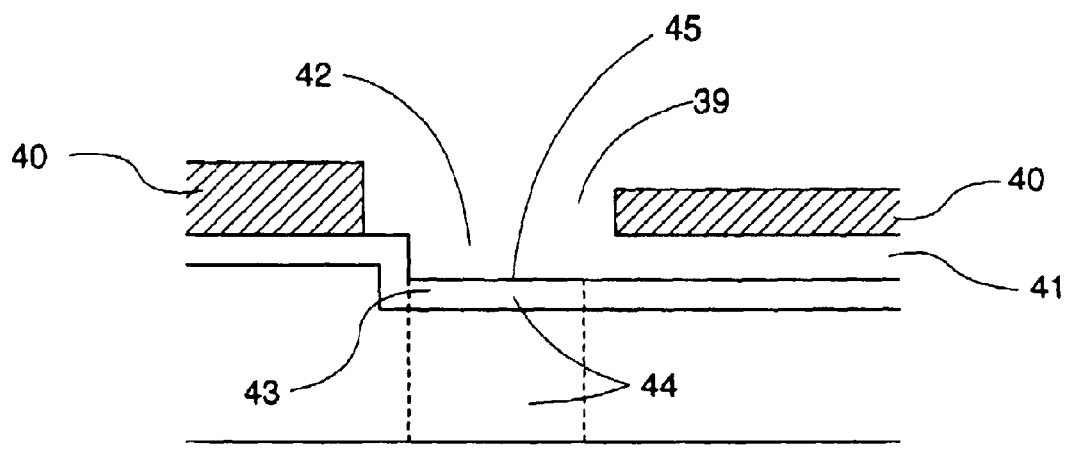

FIGS. 7a–b illustrate a variant of an EDI-port with a transparent lid (seen from above and in a cross-sectional sideview, respectively).

DETAILED DESCRIPTION OF THE INNOVATIVE MICROFLUIDIC DEVICE

The Microfluidic Structure

The microfluidic device comprises one or more microchannel structures having an inlet port for application of a liquid sample and an MS-port for release and presentation of an MS-analyte to a mass spectrometer. These kinds of ports may coincide in a microchannel structure. There may also be separate inlet ports for application of solvents and reagents and separate outlet ports or waste chambers/cavities for withdrawal of other components that are added and/or produced in the structure. Two or more microchannel structures may have common inlet ports. Depending on the particular design of the device some of the ports may be closed during the sample treatment but opened later on, for instance in order to enable proper release and presentation of the MS-analyte.

The distance between two opposite walls in a channel is typically $\leq 1000$ $\mu$m, such as $\leq 100$ $\mu$m, or even $\leq 10$ $\mu$m, such as $\leq 1$ $\mu$m. Functional channel parts (chambers, cavities etc) typical have volumes that are $\leq 500$ $\mu$l, such as $\leq 100$ $\mu$l and even $\leq 10$ $\mu$l such as $\leq 1$ $\mu$l. In important variants these volumes may be $\leq 500$ nl such as $\leq 100$ nl or $\leq 50$ nl. The depths of these parts may be in the interval $\leq 1000$ $\mu$m such as $\leq 100$ $\mu$m such as $\leq 10$ $\mu$m or even $\leq 1$ $\mu$m. The lower limits (width and depth) are always significantly greater than the largest of the reagents and analytes (including fragments and derivatives) that are to be transported within the microchannel structure. The lower limits of the different channel parts are typically in the range 0.1–0.01 $\mu$m. The aspect ratio (depth to width) may be $\geq 1$ or $\leq 1$ in all parts or in only a part of a microchannel structure.

Preferred microfluidic devices typically comprise one, two or more, preferably more than 5, microchannel structures fabricated wholly or partly in the surface of a planar substrate. In the preferred microfluidic devices of the invention, the side of the substrate in which the microchannels are located (microchannel side) may be covered by a lid comprising remaining parts, if any, of the microchannel structure. When the lid is properly mated to the upper side of the substrate, parts of the microchannel structures in the lid, if any, match the structures in the microchannel side thereby completing the microchannel structures of the device. The lid will prevent or minimise undesired evaporation of liquids as well as facilitate transport of liquids.

Each microchannel structure preferably extends in a common plane of the planar substrate material. In addition there may be extensions in other directions, primarily perpendicular to the common plane. Such other extensions may function as sample or liquid application areas or connections to other microchannel structures that are not located in the common plane, for instance.

The microfluidic devices may be disc-formed and have various geometries, with the circular form being the preferred variant (CD-form). Other variants of discs may have an axis of symmetry that is at least 3- or at least 6-numbered.

On devices having circular forms or an axis of symmetry as mentioned in the previous paragraph, each microchannel structures may be oriented radially around a central axis with an intended flow direction for each structure from an inner application area (inlet port) towards the periphery of the disc. The arrangement may be in form of one or more concentric circles (annular/circular arrangements). According to the first aspect of the invention the liquid is transported by inertia force, for instance centrifugal force, in at least a part of a microchannel structure. Examples of other ways of transportation are by capillary action, hydrodynamically, electrokinetically etc. These alternatives may also be combined with inertia force in line with what has been discussed for the first aspect of the invention.

Each microchannel structure comprises one or more channels in the microformat. The channels may comprise chambers/cavities that are in the microformat. Different parts of a structure may have different discrete functions. In addition to the channel parts mentioned above (inlet port, MS-port, transportation conduit/channel), there may be one or more channel parts that function as (a) application zone/port for reagents and liquids other than sample liquid (second inlet port), (b) additional MS-ports, (c) reaction zone, for instance for derivatization of an analyte discussed above (digestion, tagging etc).

(d) pressure creating zone (for instance hydrostatic pressure), (e) volume defining zone, (f) mixing zone, (g) zone for separating and/or concentrating and/or purifying the analyte or a derivative or fragment thereof, for instance by capillary electrophoresis, chromatography and the like, (h) waste conduit/chamber/cavity (for instance in the form of an outlet port), (i) zone for splitting a liquid flow, etc.

These kinds of zones may be present as distinct chambers or conduits that may have a cross-sectional dimension that differs from a preceding and/or a subsequent part of the microchannel structure.

Splitting may be located at the inlet so that a starting sample is divided in several aliquots, each of which is processed in parallel within a structure.

Except for the presence of an MS-port this kind of microchannel structures have been described in a number of previous patent publications. See the background publications discussed above.

Between parts having different functions there may be valves that can be overcome by increasing the force driving the liquid. For variants utilizing spinning, this may for instance be accomplished by increasing the spinning and/or utilizing pressure built up within the WO 0040750 (Gyros AB) and WO 0146465 (Gyros AB). Valves may be structure due to addition of a new portion of liquid combined with spinning. See for instance based on capillary junctions (WO 9807019 (Gamera Bioscience)) or hydrophobic breaks (WO 9958245 (Gyros AB) or on thermic properties of the valve material. The latter kind of valves may be illustrated by so called sacrificing valves (WO 9853311 (Gamera Bioscience)) for instance containing a plug of wax-like material, or reversible valves, for instance containing a thermoreversible polymer in the form of a plug (WO 0102737 (Gyros AB)).

One kind of versatile microchannel structures used according to the invention comprise a zone in which separation and/or concentration and/or a purification of the analyte or an analyte-derived entity can take place. This zone is located either before or in the MS-port. Examples of analyte-derived entities are fragments and derivatives of the analyte. This kind of functionality may be particularly important for samples containing low concentrations of analytes, complex mixtures of analytes or high concentrations of interfering substances that may negatively affect the resolution and/or sensitivity of the MS-analyte when analyzed by mass spectrometry. Separation and/or concentration and/or purification of the sample analyte or analyte-derived entities can be accomplished according to similar principles as typically employed in the life science area, i.e. separations based on size exclusion and/or on differences in binding to a ligand structure are applicable. Accordingly, this kind of channel part may contain a separation medium that is capable of binding the analyte or an analyte-derived entity but not to the contaminants, or vice versa. The separation medium is typically in particle/bead form, or attached on the surface of the separation zone or in the form of a monolithic plug that permits through flow. If the analyte or the analyte-derived entity becomes bound, a liquid having the proper desorption characteristics for the bound entity is subsequently allowed to pass through the chamber whereupon the bound entity is released and transported downstream. This transport may be directly to the MS-port or to a zone in which a further preparation step is accomplished. Washing steps may be inserted between the sample liquid and the desorption liquid. The separation medium may be soluble or insoluble during the binding step. Soluble separation media are typically insolubilized after binding according to principles well-known in the field of macrosopic separations.

Binding to the separation medium may involve formation of covalent bonds or encompass affinity binding. Binding of covalent nature for this purpose is typically reversible, for instance by thiol-disulfide exchange, such as between a thiol-containing analyte or analyte-derived entity and a separation medium containing a so called reactive disulfide, or vice versa. Affinity binding, including adsorption, can be illustrated with:

(a) electrostatic interaction that typically requires that the ligand and the entity to be bound have opposite charges, (b) hydrophobic interaction that typically requires that the ligand and the entity to be bound comprises hydrophobic groups, (c) electron-donor acceptor interaction that typically requires that the ligand and the entity to be bound have an electron-acceptor and electron-donor group, respectively, or vice versa, and (d) bioaffinity binding including other kinds of binding in which the interaction is of complex nature, typically involving a mixture of several different kinds of interactions and/or groups.

Ion exchange ligands may be cationic (=anion exchange ligands) or anionic (=cation exchange ligands). Typical anion exchange ligands have a positively charged nitrogen, the most common ones being primary, secondary, tertiary or quarternary ammonium ligands, and also certain amidinium groups. Typical cation exchange ligands are negatively charged carboxylate groups, phosphate groups, phosphonate groups, sulphate groups and sulphonate groups.

Bioaffinity binding includes that the analyte or the analyte-derived entity is a member of a so-called bioaffinity pair and the ligand is the other member of the pair. Typical bioaffinity pairs are antigen/hapten and an antibody/antigen binding fragment of the antibody; complementary nucleic acids; immunoglobulin-binding protein and immunoglobulin (for instance IgG or an Fc-part thereof and protein A or G), lectin and the corresponding carbohydrate, etc. The term "bioaffinity pair" includes affinity pairs in which one or both of the members are synthetic, for instance mimicking a native member of a bioaffinity pair.

If the analytes in a sample have peptide structure or nucleic acid structure or in other ways have a pronounced hydrophobicity, the separation medium may be of the reverse phase type (hydrophobic) combined with using desorption liquids (eluents) that are organic, for instance acetonitrile, isopropanol, methanol, and the like. Depending on the particular sample and the presence of analytes or analyte-derived entities, which have a common binding structure, a group-specific separation medium may be utilized for the kind of separations discussed above. The separation medium may thus, like a reverse phase adsorbent, result in an MS-sample that has a reduced concentration of salt, i.e. in desalting.

In each microchannel structure there may be two or more separations zone. In this case the zones typically seaparate according to different principles such as size and charge. For amphoteric substances such as proteins and peptides the latter principle may be illustrated with isoelectric focusing.

By using a separation zone it is possible to concentrate the sample such that the concentration of an analyte or an analyte-derived entity in the desorption liquid after passage of the separation medium is higher than in the starting sample. The increase be with a factor $>10^0$ and may typically be found in the interval $10^1-10^6$, such as $10^1-10^4$.

As already mentioned a separation zone may be combined with zones for derivatization. There may also be microchannel structures that have a derivatization zone but no separation zone.

Figure 1:
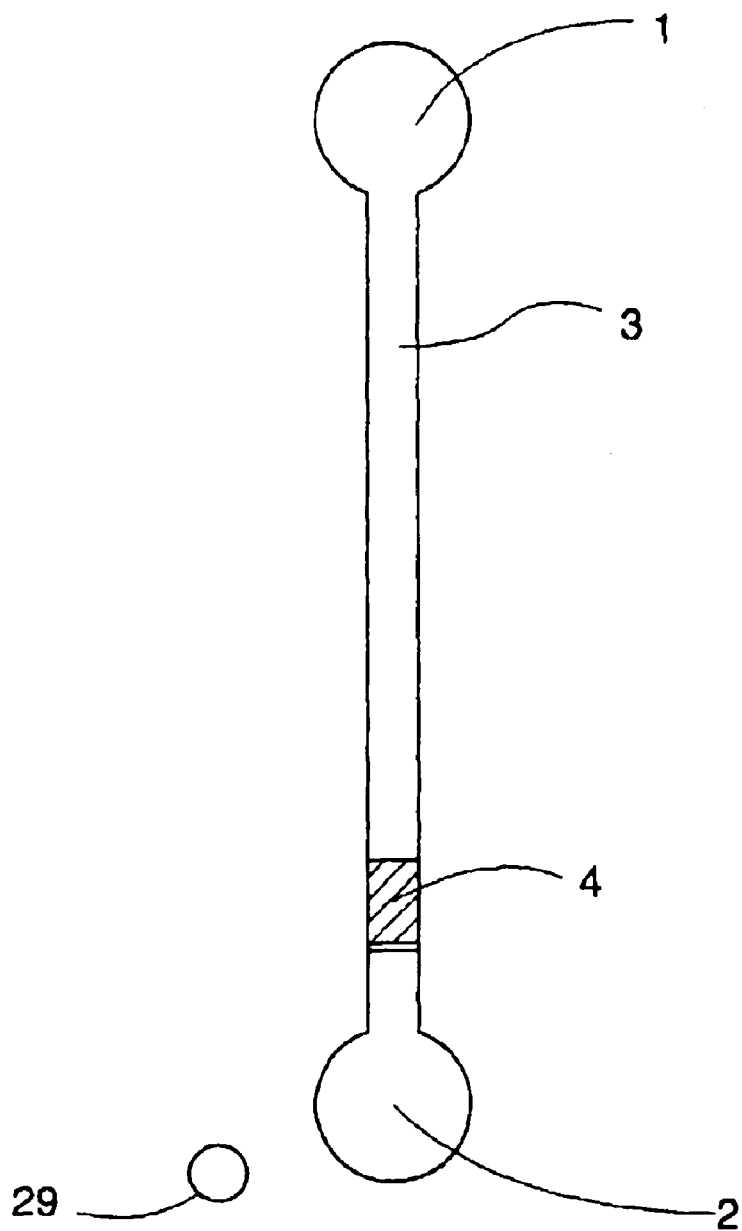
FIGS. 1–3 illustrate various microchannel structures that have an MS-port.

FIG. 1 illustrates a microchannel structure that comprises (a) an inlet port (1) for liquids including the sample liquid, (b) an MS-port (2) comprising for instance an EDI area that may be opened or closed, (c) a flow conduit (3) between the inlet port (1) and the MS-port (2). The flow conduit (3) may have a zone (4) containing an adsorbent for separation/concentration. If there are several microchannel structure in a device there may be a common application area/channel with openings for the inlet ports (not shown). The MS-port may be an EDI MS-port, an eletrospray MS-port.

The use of the structure of FIG. 1 is as indicated. By using spinning for liquid transportation into an open form of the MS-port, aqueous liquids, for instance the sample or the washing liquids, may leave the port as small drops by the centrifugal force while liquids having a lower vapor pressure may evaporate leaving the MS-analyte in the port, e.g. at a lower spinning rate.

Figure 2:
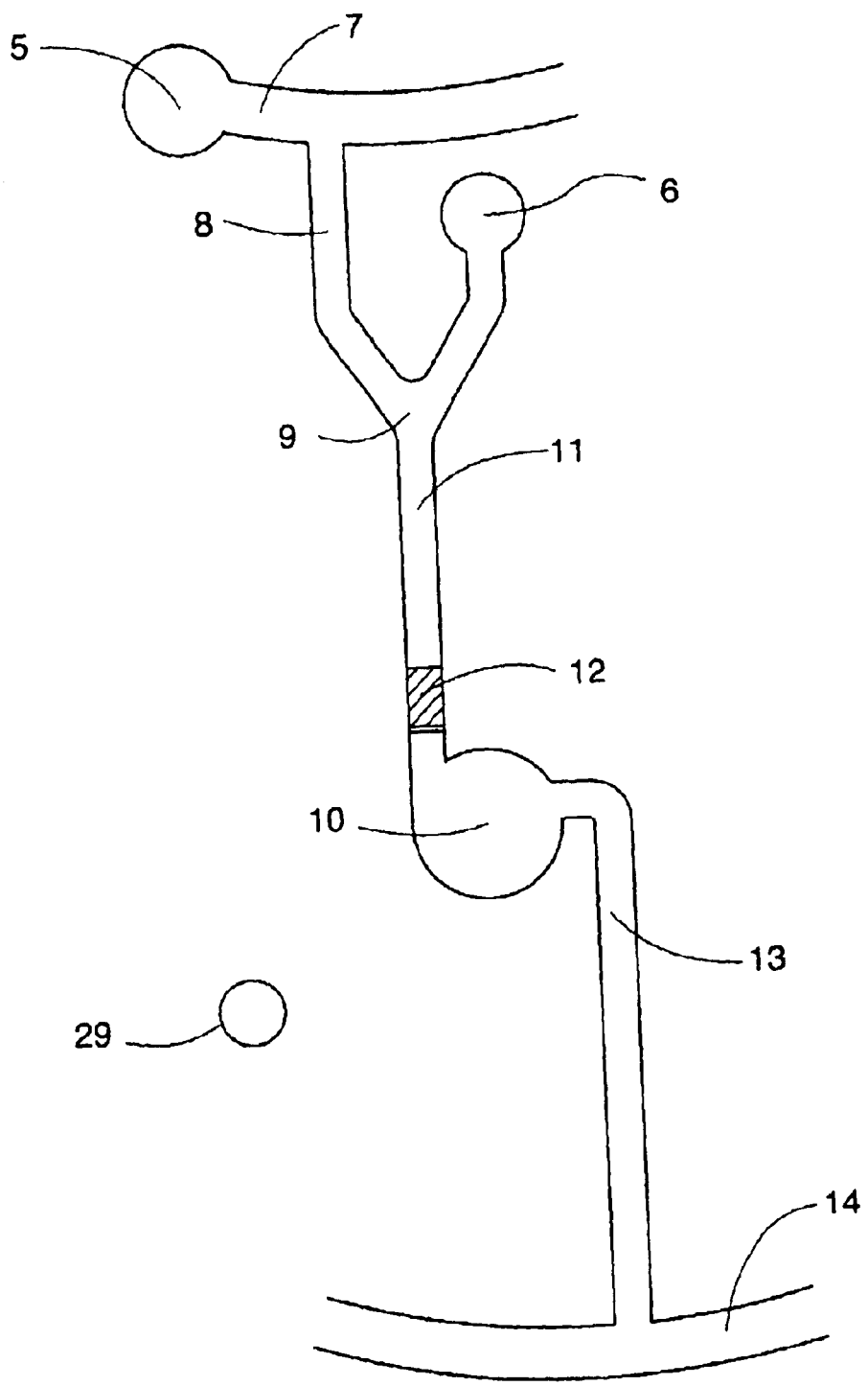

FIG. 2 illustrates another variant of a suitable microchannel structure. It has two inlet ports (5,6) that may be used for application of sample, washing liquids and desorption liquid. One of the inlet ports (5) is connected to an application area/channel (7) that may be common to several microchannel structures in the same device. This first inlet port (5) is connected to one of the shanks (8) in a U-shaped channel part via the application area/channel (2). The other inlet port (6) is connected to the other shank of the U. In the lower part of the U there is an exit conduit (9) leading to an MS-port (10). In the channel (11) between the exit conduit (9) from the U and the MS-port (10) there may be a zone (12) containing a separation medium. From the MS-port (10) there may be a waste channel (13) leading to a waste space (14) that may be common for several microchannel structures in the same device. There may be a valve function, for instance in the form of a hydrophobic break, in the exit conduit (9).

Figure 3:
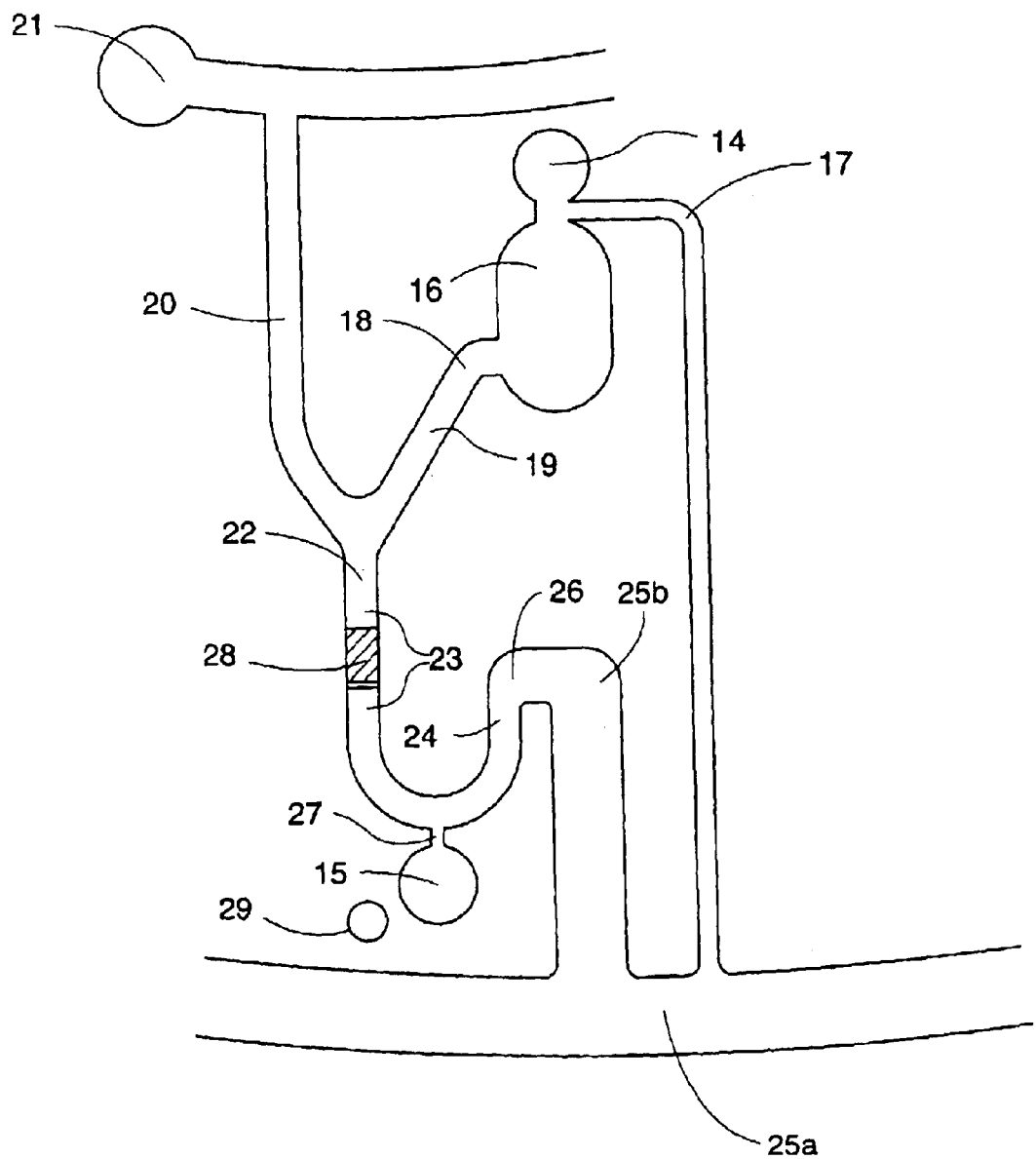

FIG. 3 illustrates another alternative of a microchannel structure which comprises a separate sample inlet port (14), an MS-port (15) and therebetween a microchannel structure that may be used for sample preparation. In this variant there is a volume-defining unit (16) between the two ports (14,15) with an over-flow conduit (17). At the lower part of the volume-defining unit (16) there is a first exit conduit (18) leading to one of the shanks (19) of U-shaped channel part. The other shank (20) of this U may be connected to an inlet port (21) for washing and desorption liquids. At the lower part of the U-shaped channel part there may be a second exit conduit (22) leading into one of the shanks (23) of a second U-shaped channel part. The other shank (24) may be connected to a waste channel (25b) that after a bent (26) may end in a waste chamber (25a). At the lower part of this second U-formed channel part there may be a third exit conduit (27) leading into the MS-port (15) that may contain an EDI area or an electrospray unit. In order to control the flow in the structure, valve functions are preferably located in the first exit conduit (18), for instance immediately downstream the volume-defining unit (16), possibly also in the second exit conduit (22), for instance immediately after the first U-shape, and in the third exit conduit (27), for instance immediately after the second U-shaped channel part. The valves may be of the types discussed above with preference for hydrophobic breaks. A suitable adsorbent (28) as discussed above may be placed in the shank (23) of the second U-shaped channel part and may also function as a valve, in case the adsorbent is in the form of particles they are preferably kept in place by a constriction of the inner walls of the conduits.

The structure presented in FIG. 3 is adapted for transporting the liquid with centrifugal forces, i.e. with the Structure present in a disc and oriented radially outwards from the center of the disc. At start the volume-defining unit (16) is filled up somewhat above the over-flow channel (17). By overcoming a valve function located in the first exit conduit (18), the liquid will pass into the first U-shaped channel part and down through the adsorbent where the analytes are captured. The remaining liquid containing non-analyte components will pass out into the waste channel (25b). In the next step, washing liquids may be applied through the inlet port (21), i.e. through the second shank (20) of the first U-shaped channel part or via the same inlet port (14) as the sample. Also these liquids will pass out into the waste channel (25b). Subsequently, a desorption liquid is applied through either of the two inlet port (14,21) and allowed to pass through the valve function in the third exit conduit (27). The desorption liquid containing released analyte or analyte-derived entities is passed downstream, for instance into the MS-port (15). The operations are preferably carried out while spinning the disc. If the valves are in the form of hydrophobic breaks they can be passed by properly adapting the g-forces, i.e. by the spinning. By properly balancing the hydrophilicity/hydrophobicity of a liquid, passage or non-passage through a valve may be controlled without changing the spinning speed. This is illustrated by utilizing a hydrophobic break as the valve in the third exit conduit (27) combined with utilizing water-solutions as samples and as washing liquids and liquids containing organic solvents as desorption liquids. In the alternative, valves that are opened by external means can be used. By placing the outlet to the first exit conduit (18) at a distance above the lowest part of the volume-defining unit (16) particulate matters, if present in the sample, will sediment and be retained in the volume-defining unit (16) when it is emptied through the first exit conduit (18).

Calibrator areas (29) are shown in each of FIGS. 1–3. Each calibrator area may be connected to a common area for application of calibrator.

The size of a volume-defining unit depends on the sample, reagents used, washing etc. and the requirement the sensitivity of the mass spectrometer sets for concentrating an analyte or an analyte-derived entity. Typical volumes of channel parts that have specific functions are in the range of 1 nl to 1000 $\mu$l, mostly below 1 $\mu$l such as below 500 nl or even below 100 nl such as below 25 or 10 nl (volume defining unit, reactor part, separation part etc). Application of aliquots of a sample to the same inlet port may replace the need for a larger volume defining unit.

These kind of flow systems has been described in WO 0040750 (Gyros AB) and WO 0146465 (Gyros AB) which are hereby incorporated by reference.

In certain variants the inlet port for the sample and the MS-port may coincide. In this case the MS-port preferably comprises the surface on which the analyte can be collected (adsorbed). Remaining liquid and washing liquids, if used, are passed into the microchannel structure that then will function as a waste channel and possibly contain a separate outlet port particularly adapted for wastes and the like, or a waste chamber. In order to accomplish a concentrating and/or separating effect the surface may expose structures selectively binding/capturing the analyte as discussed above. This variant also encompasses that there may be a separate inlet port for washing and desorption liquids and microchannel part communicating with the combined sample and MS-port.

The MS-Port

The invention the MS-port typically has conducting properties. The conducting part may be present in an EDI area or a nozzle suitable for electrospray, for instance a nanospray, or in any other form device that is used to present a sample to a mass spectrometer. An electrospray nozzle provides an orifice for instance in the form of a tip with a through-passing hole. Various kinds of sample presentation devices have been described in the publications discussed above.

There may be a valve in the microchannel before its inlet to the MS-port.

The term conducting material includes semi-conducting material, although materials having a conductivity that is larger than silicon or larger than germanium are preferred. A typical conducting material comprise (a) metals such as copper, gold, platinum etc, (b) conducting polymers including polymers that are conducting as such, and conducting composites containing a non-conducting polymer and a conducting material such as a metal or a conducting polymer, (c) other conducting composites, etc.

Electrospray Ionisation MS-Ports

Figure 4:
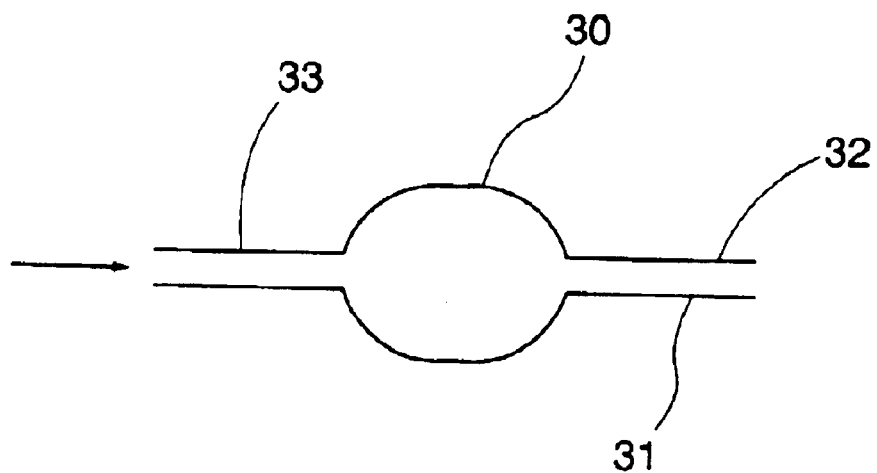
FIG. 4 illustrates an MS-port in form of an electrospray (sideview).

FIG. 4 illustrates an MS-port suitable for electrospray ionisation in a mass spectrometer. This kind of port may be located where an MS-port has been indicated in any of the structures given in FIGS. 1–3. The MS-analyte may thus be collected in an MS-port comprising a collection zone (30), which zone is in fluid communication via the electrospray conduit (31) with the outlet orifice (32). The electrospray conduit may be in the form of a tip. The MS-analyte is entering via conduit (32). As indicated in FIG. 4, orifices of the electrospray tip are preferably positioned on the edge of a disc. Typical disc-forms have been discussed above. In use an electrospray orifice is matched to the sampling orifice of a mass spectrometer and liquid in the electrospray tip (31) is sprayed into the mass spectrometer. In a preferred variant the disc is circular. The arrangement of the electrospray tips is preferably annular around the axis for spinning during preparation of the sample. The tips are preferably located in the edge of the disc and provide a radial spray direction. In the alternative the annular arrangement may by in a flat side of the disc with a spray direction out of the plane of the side and preferably also with a component that is directed radially. Annular arrangements preferably in the edge of a circular disc will simplify accurate positioning of the electrospray direction relative to the sample application opening of a mass spectrometer.

Electrospray suitable for electrospray ionization mass spectrometry (ESI MS), for instance adapted to the nanospray format, is mostly formed in capillaries made of glass or fused silica, or polymer material like silicon. The tubings are typically of cylindrical geometry with tip internal diameters in the 5–20 $\mu$m range. The word nanospray means that the liquid transferred out of the tubing is in the nanoliter per minute range. Suitable rates for transfer of liquid to the mass spectrometer can be found in the interval of 1–1000 nl/min, e.g. in the interval 10–500 nl/min. By infusion (no external force), only a few nanoliters per minute (5–25 nl/min) is transported out of the tubing while with applied external pressure 50–500 nl/min is more common.

A liquid solution suitable for ESI MS analysis consist of an organic solvent:water mixture including a lower concentration of acid or base. The composition of the solvent is important especially with regard to surface tension and conductivity. A low surface tension and conductivity is desirable as-to obtain an efficient desolvation and ionization process as well as a stable spray. If the sample is dissolved in water only, a so-called make-up solvent is preferably added (external delivery) to aid in the above mentioned process. A make-up solvent is typically configured co-axially (sheat-flow) around the nanospray tip. A make-up gas (typical $N_2$) is sometimes added (e.g., co-axially) as to aid in the desolvation process. Creation of a suitable liquid composition of the MS-sample may also be part of the sample preparation process taking place upstream the MS port in other parts of a microchannel structure.

The tip geometry is important as to obtain a stable spray. Preferably the tip is pulled from the cylindrical tubing whereby the tip becomes oblong with a conical shape. The outer diameter of the tubing near the orifice of the tip then becomes of similar dimension as the internal diameter.

In order to induce a spray from the capillary (towards the inlet of the mass spectrometer) a voltage has to be applied on the electrospray tip. Therefore the tip has to be made conductive. Different kind of metals can be deposited by different techniques onto the tip (or part of the tubing). Important aspects here regard the stability (life-time) of the metallized tip since the voltage applied as well as different solvents affects its stability. Other possibilities also exist than metalization, e.g., an electrode can be inserted into the tip whereby a voltage can be applied to induce electrospray. Another alternative is to make the tip in a material comprising any of the above-mentioned conducting materials. Typical voltages used in nanospray range between 500–2000 volts.

Typical electrospray nozzles are available from a number of manufacturers, for instance New Objective, MA, U.S.A. A variant that is believed to have advantages for microfluidic devices is presented in WO 0247913 (Gyros AB). See also WO 9704297 (Karger et al), U.S. Pat. No. 5,969,353 (Hsieh) and U.S. Pat. No. 6,110,343 (Ramsey et al) discussed above.

EDI MS-Ports

The MS-port may also be used for EDI-MS and will then contain an EDI-area. Upward and downward directions as used in the context of EDI areas refer to the directions defined in the figures irrespective of how the area is positioned in a mass spectrometer.

The term "EDI area" encompasses the surface of the area as well as any part of the device, which is straight under the surface.

EDI MS ports may be adapted to anyone of the different EDI mass spectrometry variants, for instance Time of Flight (TOF), Quadropole, Fourier-Transformed Ion Cyclotron Resonance (FT-ICR), ion trap etc.

EDI ports need a free opening for the release of the ions created during desorption/ionisation. This means that the opening typically is placed straight above the surface of an EDI area and has an area that should be coaxial with and covering the surface. This includes that the opening may be closed during the sample treatment within the microfluidic device but subsequently opened to enable irradiation and desorption/ionisation and possibly also evaporation of solvents. If an IDI principle is used the opening should also provide space for the incident irradiation.

An EDI area may in principle have any geometric form although preferred forms should be as compact as possible. Regular forms, such as squares and square-like forms, and rounded forms, such as circular and circle-like forms. The size of an EDI area preferably is the same as a circle with a diameter in the interval of 25–2000 µm. For IDI there may be advantages if the cross-sectional area of the incident beam is able to encompass the complete surface of an IDI area or as much as possible, for instance more than 25% or more than 50%.

An EDI area comprises a conducting layer (layer I), for instance a metal layer of copper, gold, platinum, stainless steel etc or a layer of any other conducting material of the kinds discussed above. Layer (I) is many times essentially planar and may coincide with the surface of the EDI area or be parallel thereto. The complete area from the lowest part to the most upper part may be made of conducting material, i.e. correspond to layer (I). In the case the microfluidic device comprises more than one microchannel structure with an EDI MS-port, layer (I) of one EDI area may extend into and encompass layer (I) in two or more of the other EDI areas, with preference for all of them. Layer (I) of all EDI areas of a device may be part of a common conducting layer, which may be essentially planar and possibly with depressions corresponding to the EDI areas and/or to other parts of the microchannel structures of the innovative device. The exact geometric shape of layer (I) outside the MS-port may differ depending on the particular device and practical ways of its manufacture. For instance a common conducting layer may have an annular form in case the MS-ports are annularly arranged, i.e. only be present in EDI areas of a certain distance from a the center of the arrangement.

In one innovative variant, there is a non-conducting layer (layer (II)), which covers the conducting layer (I). Layer (II) in one EDI area may extend into and encompass layer (I) in two or more of the other EDI areas as described for layer (I).

In another innovative variant the device have a conducting layer (III) positioned above the common plane defined by the surface of each EDI area of a device. Layer (III) has openings matching the surfaces of the EDI areas and permitting irradiation of the EDI surfaces and escape of ions produced through the openings.

These innovative variants of EDI areas are schematically illustrated in FIGS. 5a–f, each of which shows a cross-sectional view across the EDI areas of two EDI MS-ports in a microfluidic device according to the invention. The EDI surfaces are referenced as (51) and the EDI areas as (52) within the dotted vertical lines). Each EDI port comprises the EDI area plus the corresponding depression. The conducting layers (54) are hatched. It is apparent that each EDI area comprises a conducting layer (I) (53).

Figure 5A:
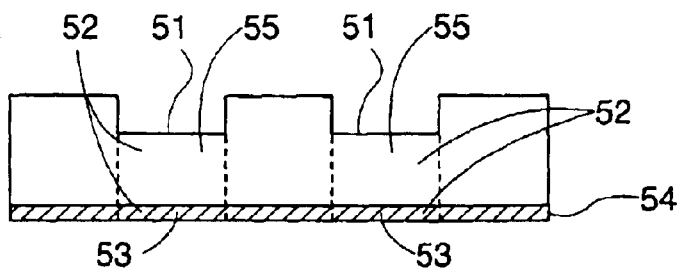
Figure 5B:
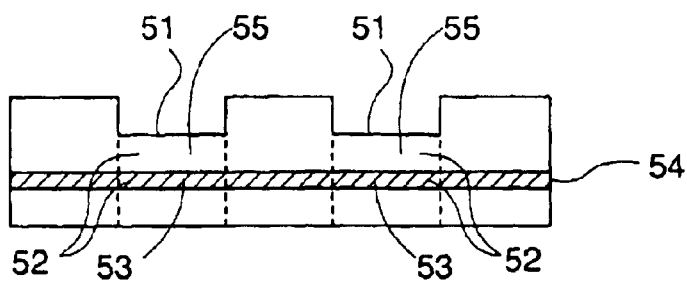
Figure 5C:
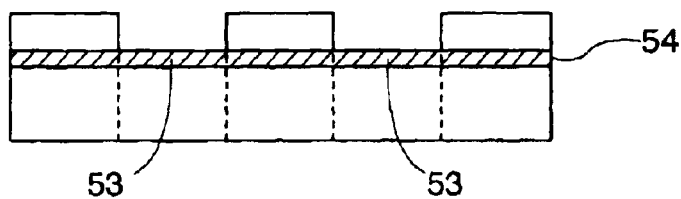
Figure 5D:
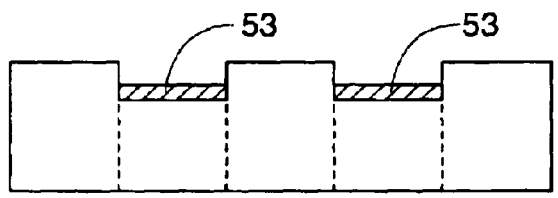
Figure 5E:
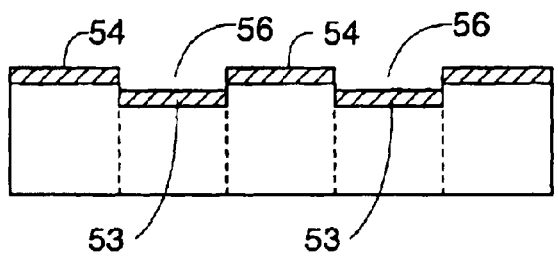
Figure 5F:
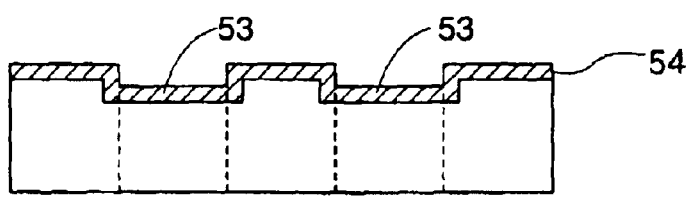

FIG. 5a shows a common conducting layer (54) at the bottom of the device which layer encompasses layer (1) (53) of each EDI area (52). A non-conducting layer (U) (55) is placed between layer (I) (53) and the EDI surface (51). FIG. 5I, shows a variant, which is similar to the variant in FIG. 5a, but the common conducting layer is embedded within the material from which the device is fabricated. Layer (II) (55) is present. In FIG. 5c there is a common conducting layer (54) Comprising the upper surfaces of the EDI areas. In FIG. 5d there is no common conducting layer. Layer (I) is in the upper surfaces of the EDI areas. The different layers (I) (53) are isolated from each other. FIG. 5e shows a variant in which there is a continuous conducting layer (54) above layer (I) (53) of the EDI areas. This conducting layer (54) has openings (56) corresponding to the openings of each MS-port and may be the surface of the upper or lower side of a lid covering the microchannel structure (the lid is not shown). FIG. 5f shows a variant in which there is a common continuous conductive layer comprising layer (I). Layer (I) corresponds to the EDI surfaces. The continuous layer also encompasses the walls of the depressions in the EDI ports.

In one variant all the material of the body in which the microchannel structures are fabricated is the same as in layer (I), i.e. there may be no non-conducting material present, except for the lid.

FIG. 6 illustrates an arrangement for EDI MS-ports on a circular disc (with a transparent lid), in which layer (I) (34) of each EDI surface has a conductive connection (35) with a peripherial conductive layer (36) at the edge of the disc. In the variant shown in this figure each microchannel structure (37) extends upstream to an inlet port (38).

FIGS. 7a–b illustrate an EDI MS-port which the opening to the EDI surface is defined by a hole (39) in a lid (40) which in this case is transparent. One can see the incoming crochannel (41), which opens to a circular depression (42) with a diameter, which is less than the diameter of the hole (39). Layer (I) (43), EDI area (44, between the dotted lines), EDI surface (45) are shown. The conductive layer extends from layer (I). This design in which the MS-port provides an opening which is greater than the EDI area will facilitate for an incident beam to cover any spot of the EDI surface.

A conductive layer per se may function as a conductive connection or there may be distinct connections (35) to layer (I). See FIG. 6.

A lid used to cover the microchannel structure may also cover the EDI areas or restrict them from exposure to the ambient atmosphere. In this case there may be advantages if the lid is removable at least around the EDI areas. Thus after treatment in upstream parts of the microchannel structure, the EDI areas can be exposed for evaporation of solvents that may be retained thereon or for irradiation in order to accomplish desorption/ionisation of MS-analyte molecules.

The Method Steps of the First Aspect of the Invention

When the innovative device is used, the necessary reagents and/or the sample including the analyte are applied to the appropriate inlet ports (application areas) and transported downstream in the structure by an applied liquid flow or transportation mechanism as discussed above. The liquid flow or transport may be paused when a reagent and/or an analyte have reached a predetermined part in which the sample is subjected to a certain procedure, for instance capillary electrophoresis in a separation part, a chemical reaction in a reaction part, selective adsorption in a concentrating part, detection in a detection part, evaporation and/or crystallization in an EDI MS-port, collection of the appropriate liquid for electrospray ionisation in an electrospray ionisation MS-port, etc.

During transport through a microchannel structure the solvent composition may be changed to fit the particular kind of MS-port used. In the case the MS-port is an EDI MS-port and the microchannel structure contains a separation medium, an EDI matrix may be (a) included in the desorption liquid or in a subsequent liquid passing through at least a part of the microchannel structure, (b) predispensed to the EDI surface or dispensed after the analyte has been deposited on the surface, or (c) introduced via a separate microchannel downstream the separation medium. There may also be included substances that facilitate crystallization on the EDI surface.

Calibration of the Mass Scale

To ensure accurate mass determination, calibrator areas (spots) containing a compound of known molecular weight (standard) may present in the proximity of the EDI MS-ports. Calibrator areas (29) are shown in FIGS. 1–3. Alternatively, the standards may be included in the sample or added to the EDI area before desorption/ionisation (internal calibrator). The choice of calibrator substance, its amount etc will depend on its use as an external or internal calibrator, the MS-analyte and its concentration etc.

Material From Which the Microfluidic Device is Manufactured

The microchannel structures are typically fabricated in inorganic and/or organic material, preferably plastics or other organic polymers. The material may be conducting or non-conducting as already discussed. Certain parts of a microchannel structure may be metalized.

Suitable organic polymers may derive from polymerisation of monomers comprising unsaturation such as carbon—carbon double bonds and/or carbon-carbon-triple bonds. The monomers may, for instance, be selected from mono-, di and poly/oligo-unsaturated compounds, e.g. vinyl compounds and other compounds containing unsaturation.

Another type of organic polymers that may fit are based on condensation polymers in which the monomers are selected from compounds exhibiting two or more groups selected among amino, hydroxy, carboxy etc groups. The plastics contemplated are typically polycarbonates, polyamides, polyamines, polyethers etc. Polyethers include the corresponding silicon analogues, such as silicone rubber.

The polymers of the plastics are preferably in cross-linked form.

The plastics may be a mixture of two or more different polymer(s)/copolymer(s).

At least a part of the microchannel structure may have a surface that has been derivatised and/or hydrophilized, for instance by being coated with a non-ionic hydrophilic polymer according to the principles outlined in International Patent Publication WO 0147637 (Gyros AB). This also includes functionalisation in order to introduce one or more structures that are capable of interacting with the sample analyte or with one or more of the reagents added. Surfaces may be made of copper, gold, platinum, stainless less etc, for instance by metallization, in order to enable a desired derivatization or for providing a conducting surface, for instance in an MS-port. Gold surfaces for instance may be derivatized by reaction with thiol-containing compounds that have a desired functionality, for instance hydrophilicity.

The optimal water contact angle for the surfaces within a structure depends on the protocols to be carried out, the dimensions of the microchannels and chambers, composition and surface tension of the liquids, etc. As a rule of thumb, at least one surface of the microchannel structure (wall, bottom or top), should provide a water contact angle that is $\leq 40°$ or $\leq 30°$, such as $\leq 25°$ or $\leq 20°$. These figures refer to values obtained at the temperature of use, primarily room temperature.

It is believed that the preferred variants of the inventive microfluidic devices will be delivered to the customer in a dried state. The surfaces of the microchannel structures of the device therefore should have a hydrophilicity sufficient to permit the aqueous liquid to be used to penetrate the different parts of the channels of the structure by capillary forces (self-suction). This of course only applies if a valve function at the entrance of the particular part has been overcome.

Best Mode

The best mass spectrometric results so far accomplished have been with the variant described in example 4 below. It is believed that there are advantages by going over to more complex fluidic structures as illustrated in FIGS. 2 and 3, and more complex designs of the EDI surface and the channel outlets as illustrated in FIG. 7.

The invention is further defined in the appending claim and will now be illustrated with a non-limiting experimental part.

EXAMPLE 1

Gold at Different Positions in a CD

| Gold patterning | Sensitivity* | Charging of substrate** |
|---|---|---|
| No gold | Poor | Yes |
| Gold on all sides | Good | No |
| Gold on upper side | Good | No |
| Gold on bottom side | Good | Yes |
| Isolated gold spots on the upper side | Good | Yes |
| Gold spots on the upper side. Every spot being conductively connected contact with the adapter plate through an individual gold string or a common gold area. | Good | No |

*Good = sensitivity for a in-solution tryptic digest of BSA comparable to the sensitivity obtained on a conventional stainless steel target
**Charging is observed as significant mass shift ( $\geq$ 1 Da) upon repeated laser desorption/ionization and/or loss of signal.

This table shows the results form a summary of experiments performed in order to optimise the design of the CD-MALDI interface. Gold was sputtered at various positions of the CD and the MALDI characteristics were studied for a tryptic digest of Bovine Serum Albumin (BSA). The CD was placed on a metal adapter inserted into the ion source. The gold was hence patterned in various ways to determine the importance of electrical contact between the MALDI ports and the adapter plate.

EXAMPLE 2

Testing of Crystallization on the MALDI Surface

Microfluidic device: The CD was fabricated of polycarbonate. Each microchannel structure in the CD only contained an inlet port (uppstreams), the ms-port (downstreams) and a flow conduit between. The inlet and ms-port consisted of open areas made by drilling holes in the lid before covering the CD with the lid, i.e., the open areas on the CD was in contact with the surrounding atmosphere. Only a minor part of the flow conduit at the ms-port was in connection to the open area. The width and the depth of the microchannel leading into the ms-port were 100 µm and 40 µm, respectively. The open area of the ms-port had a cylindrical geometry with a diameter of 300 µm (drilled hole) and depth 70 µm., where the depth is the thickness of the lid. The bottom of the open area, therefore, constituted of the upper surface of the CD (and a minor part of the microfluidic channel) while the walls surrounding the open area, and restricting the dimension of the ms-port, was defined by the hole in the lid. The CD was metallized with gold (gold-sputtering) only on the side opposite to the microchannel structures.

Experimental: 100 nl of a sample consisting of two peptides, Angiotensin II (Mw 1046.2) and Bradykinin (Mw 1060.2), 20 fmol/µl each, dissolved in 50% isopropanol saturated with α-cyanohydroxycinnamic acid (+0.1% trifluoroacetic acid) was applied in the inlet hole by pipetting and transported to the open area by spinning (500 rpm). The CD was thereafter cut in half and the part containing the samples to be analysed was fixed by metal-screws onto a MALDI target probe adapted to contain on half of the CD. The probe was a Bruker standard target in the 96 well format. The CD + probe was then inserted into a Bruker Biflex MALDI time-of-flight (TOF) apparatus for mass spectrometry analysis.

Results

The sample liquid was slowly transported out into the open area (500 rpm). Once reaching the open area the solvent quickly evaporated and crystallization started. Crystals could been seen as dark spots in the open area of the ms-port. The volume of the ms-port was 5 nl while the sample applied was 100 nl. Since the volume transported out into the open area per time unit was less than 5 nl and solvent evaporation per time unit was faster than the incoming volume no overflooding in the ms-port was taking place. Therefore, the sample volume applied can far exceed the volume of the ms-port whereby the sample can be concentrated therein.

A high mass resolution was obtained since the peptide peaks were isotopically resolved. The peptide masses deviated slightly (less then 1 Dalton) from their theoretical values, but no calibration was performed. Also, the detection sensitivity has to be considered high since low femtomoles of peptides were detected (signal-over-noise ratio of 10) which is typically seen only in optimized MALDI TOF analysis.

EXAMPLE 3

Planar CD and Structured Removable Lid

This example shows a planar CD in combination with a lid in which the microfluidic structures are present. The structured lid was achieved through casting Memosil (Hereaus, Germany) against a nickel-coated master. The microfluidic structure employed in this example is shown in FIG. 2.

The structured lid is attached to the CD by adhesion forces. The surface facing the lid should be hydrophilic as the presented invention utilizes capillary action to fill the microfluidic structures. This is especially important as the moulded lid, being a type of silicon rubber is hydrophobic.

The upper side of the CD was covered with gold using a DC Bias magnetron sputtering method ($1* 10-5$ tort, Ar plasma and titan as adhesion layer) and made hydrophilic according to the following procedure; The gold sputtered side was cleaned by rinsing with ethanol, followed by an oxygen plasma treatment (Plasma Science PSO500,). After plasma cleaning a self-assembled monolayer (SAM) of hydroxylthiol was formed on the gold surface. The hydroxylthiol was 11-mercapto-1-undecanol (Aldrich, Milwaukee, Wis.) and used at a concentration of 2 mM in degassed ethanol. To obtain a well-organized SAM, the gold sputtered disc was immersed in the thiol solution over night. After the thiol adsorption the CD was sonicated in ethanol for ca 2 min.

The lid, containing the microfluidic channels, was attached to the CD by adhesion forces. A second piece of polymeric material was mounted at a position of 180° from the structured lid as a counterbalance. Reversed phase beads (Source 15 RPC, Amersham Pharmacia Biotech, Sweden) with a diameter of 15 µm were packed into the individual structures using the filling port present in the common distribution channel. The slurry, containing the beads, was drawn into the individual channels by capillary action. Eighteen parallel reversed phase columns were formed when the disc was spun at 3000 rpm for 1 minute. The columns were rinsed with water containing 0.1% TFA (trifluoroacetic acid, Aldrich)) two times. The rinsing was performed at an rpm of 2500 for ca 1 min. 200 nL of in-solution tryptic digest of BSA was added to individual channels through the sample inlet. The following procedure was used for digestion. The BSA (Sigma) was dissolved to a final concentration of 4.75 pmol/µl in 0,1 ammoniumbicarbonate buffer at pH8. The enzyme-modified trypsin (Promega Corp., Madison, Wis.) was added and dissolved at a ratio of BSA/trypsin 20:1. The sample was incubated at 37° for 4 hours and then stored at −20° C. until used.

The sample was allowed to pass over the reversed phase columns at 1500 rpm. A second rinsing/washing step was performed as above using water containing 0.1% TFA. Finally the peptides were eluted using 200 nL eluent consisting 50% isopropanol, 50% water and (α-cyano-4-hydroxycinnamic acid (Aldrich) below saturation. The eluent was prepared by saturating a water:isopropanol (50%) mixture with α-cyano-4-hydroxycinnamic acid. To 100 µL of this mixture 200 µL of 50% water:50% isopropanol was added, resulting in an eluent saturated to approximately $\frac{2}{3}$ with α-cyano-4-hydroxycinnamic acid.

The presentation of the sample in the MALDI port was performed in two different ways.
  a) In the first example a full structure was utilised (FIG. 2). Eluent from the column was collected in the container placed at an outer radial position relative of the reversed phase column. When the lid was removed the liquid quickly evaporated leaving co-crystallized matrix and peptides on the gold sputtered surface. The disc was cut in halves to fit in the MALDI ionisation interface.
  b) The moulded structure was cut directly after the packed column leaving an open-ended microstucture. The eluent was allowed to pass the column at a predetermined speed (1500 rpm) in order to generate a controlled evaporation of the solvent at the MALDI port, and hence the formation of co-crystallized matrix and peptides suitable for MALDI analysis. The disc was cut in halves to fit in the MALDI ionisation interface.

EXAMPLE 4

Structured CD and Site-Specific Elution

This example employs a CD with integrated microfluidic structures, a thin (≤70 μm) lid with holes at positions matching the MALDI port in the CD. The microfluidic structure employed in this example is shown in FIG. 1.

The polycarbonate CD was covered with gold as described above. The side was hydrophilized using the thiolprocedure described above. The lid (SkultunaFlexible, Skultuna, Sweden), having, pre-drilled holes, was attached to the CD through heat pressing at 135° C.

Reversed phase beads (Source 15 RPC) with a diameter of 15 μm were packed in the individual structures using capillary forces in combination with centrifigation. The columns were rinsed with ethanol and spun to dryness before 23 fmol of tryptically digested BSA was added and spun down using 700 rpm. The tryptic digest of BSA was generated according to the procedure described above. After sample addition, the column was rinsed twice with water. α-cyano-4-hydroxycinnamic acid was mixed in an organic solvent of acetonitril/water 3:7 containing 0,1% TFA to a saturation of ⅔ and 250 nl was used to elute the sample from the 3 nl packed column.

The crystals obtained after evaporation of the organic/water mixture contained co-crystallized peptides. Eight singly charged peptide peaks were present in the mass spectrum obtained

What is claimed is:

1. A microfluidic device in the foam of a disc comprising one, two or more MS-ports for the presentation of an MS-analyte to an EDI-MS apparatus, wherein each of said MS-ports being part of a microchannel structure comprising an inlet port for a sample, wherein each of said microchannel structures are oriented radially in the disc and arranged annularly around a spinning axis of the disc; and comprising an area (EDI area) for presenting the MS-analyte to a mass spectrometer, said EDI area comprising a layer I of conducting material having a conductive connection and/or a calibrator area in the proximity of the MS-port.

2. The microfluidic device of claim 1, wherein there are two or more EDI areas and layer (I) of each EDI area is part of a common continuous conducting layer.

3. The microfluidic device of claim 1, wherein layer (I) it covered by a non-conducting layer (layer II).

4. The microfluidic device of claim 3, wherein there are two or more EDI areas and layer (U) of each EDI area is part of a common continuous non-conducting layer.

5. The microfluidic device of claim 1, wherein layer (1) is exposed in the MS-port at the surface of the EDI area, or embedded in the EDI area below said surface, or exposed at the bottom of the device.

6. The microfluidic device of claim 1, wherein the microchannel structuresare covered by a lid which may or may not have an opening above an EDI area.

7. The microfluidic device of claim 6, wherein said lid is removable.

8. The microfluidic device of claim 6, wherein said lid comprises a common conducting layer including the connection for electricity and an opening above each of the EDI areas.

9. The microfluidic device of claim 1, wherein the sample inlet port is at an inner position and the MS-post it at an outer position in each of said microchannel structures.

10. The microfluidic device of claim 1, wherein EDI is LDI.

11. The microfluidic device of claim 10, wherein LDI is MALDI.

* * * * *

UNITED STATES PATENT AND TRADEMARK OFFICE
CERTIFICATE OF CORRECTION

PATENT NO. : 6,717,136 B2
DATED : April 6, 2004
INVENTOR(S) : Per Andersson et al.

It is certified that error appears in the above-identified patent and that said Letters Patent is hereby corrected as shown below:

<u>Title page,</u>
Item [75], Inventors, delete "Sussanne" and replace with -- Susanne --.

<u>Column 19,</u>
Line 31, delete "foam" and replace with -- form --.

Signed and Sealed this

Fifteenth Day of March, 2005

JON W. DUDAS
*Director of the United States Patent and Trademark Office*